(12) United States Patent
Gupta et al.

(10) Patent No.: US 10,617,344 B2
(45) Date of Patent: Apr. 14, 2020

(54) DEVICE WITH INTEGRATED ALLERGY TESTING

(71) Applicant: Teleflex Medical Incorporated, Durham, NC (US)

(72) Inventors: Nisha Gupta, Audubon, PA (US); David T. Rowe, Sinking Spring, PA (US); Rodney W. Denlinger, Lancaster, PA (US)

(73) Assignee: Teleflex Medical Incorporated, Research Triangle Park, NC (US)

( * ) Notice: Subject to any disclaimer, the term of this patent is extended or adjusted under 35 U.S.C. 154(b) by 187 days.

(21) Appl. No.: 15/385,989

(22) Filed: Dec. 21, 2016

(65) Prior Publication Data
US 2017/0100070 A1 Apr. 13, 2017

Related U.S. Application Data

(63) Continuation of application No. 13/689,301, filed on Nov. 29, 2012, now Pat. No. 9,554,736.

(60) Provisional application No. 61/564,593, filed on Nov. 29, 2011.

(51) Int. Cl.
| *A61B 5/00* | (2006.01) |
| *A61B 5/145* | (2006.01) |
| *A61B 5/153* | (2006.01) |
| *A61B 5/157* | (2006.01) |

(52) U.S. Cl.
CPC .......... *A61B 5/411* (2013.01); *A61B 5/14546* (2013.01); *A61B 5/153* (2013.01); *A61B 5/157* (2013.01)

(58) Field of Classification Search
CPC ......... A61B 5/411; A61B 5/157; A61B 5/153; A61B 5/14546; A61B 10/0045; A61B 10/02; A61B 10/0266; A61B 2010/0006; A61B 17/32053; A61B 10/0096; G01N 1/02; G01N 2001/028; B01L 3/5029; B01L 2300/0663; B01L 2400/0487; B01L 2300/0864; B01L 2300/0681; B01L 2400/0406; B01L 3/50825; A61F 13/38; Y10T 436/25
See application file for complete search history.

(56) References Cited

U.S. PATENT DOCUMENTS

| 4,376,110 A | 3/1983 | David et al. |
| 4,627,445 A | 12/1986 | Garcia et al. |
| 4,703,017 A | 10/1987 | Campbell et al. |

(Continued)

FOREIGN PATENT DOCUMENTS

| JP | 2003527917 A | 9/2003 |
| JP | 2007532260 A | 11/2007 |

(Continued)

*Primary Examiner* — Lore R Jarrett
(74) *Attorney, Agent, or Firm* — Baker & Hostetler LLP

(57) ABSTRACT

A coupler for indicating the presence of a substance in blood is disclosed. The coupler includes a housing and a test strip. The housing has a proximal end and a distal end, and defines a hollow interior for receiving withdrawn blood. The test strip is held within the hollow interior of the housing. The housing removably couples with a medical instrument and a needle. The test strip produces a visible signal that indicates the presence or absence of the substance in the withdrawn blood. A kit including a syringe, a needle and the coupler is also disclosed.

16 Claims, 9 Drawing Sheets

(56) References Cited

U.S. PATENT DOCUMENTS

| | | | |
|---|---|---|---|
| 4,855,240 A | 8/1989 | Rosenstein et al. | |
| 4,957,637 A | 9/1990 | Cornell | |
| 5,200,312 A | 4/1993 | Oprandy | |
| 5,368,029 A | 11/1994 | Holcombe et al. | |
| 5,637,468 A | 6/1997 | Mason | |
| 5,928,200 A * | 7/1999 | Thorne | A61B 5/15003 604/195 |
| 6,503,726 B2 | 1/2003 | Anne et al. | |
| 7,262,019 B2 | 8/2007 | Kovalenko | |
| 7,438,852 B2 | 10/2008 | Tung et al. | |
| 7,544,324 B2 | 6/2009 | Tung et al. | |
| 7,629,127 B2 | 12/2009 | Hubscher | |
| 7,722,567 B2 | 5/2010 | Tal | |
| 7,910,381 B2 | 3/2011 | Ford et al. | |
| 7,938,806 B2 | 5/2011 | Fisher et al. | |
| 7,972,307 B2 | 7/2011 | Kraus et al. | |
| 7,989,217 B2 | 8/2011 | Yee et al. | |
| 8,388,907 B2 | 3/2013 | Gold et al. | |
| 2002/0103499 A1 * | 8/2002 | Perez | A61B 5/14514 606/182 |
| 2002/0143293 A1 * | 10/2002 | Francavilla | B01L 3/0275 604/116 |
| 2003/0109777 A1 | 6/2003 | Kloepfer et al. | |
| 2003/0150745 A1 | 8/2003 | Teodorczyk et al. | |
| 2004/0116830 A1 | 6/2004 | Trudeau et al. | |
| 2004/0138588 A1 | 7/2004 | Saikley et al. | |
| 2004/0210247 A1 | 10/2004 | Sonoda et al. | |
| 2005/0136479 A1 | 6/2005 | Lyng et al. | |
| 2005/0136553 A1 | 6/2005 | Kaylor et al. | |
| 2007/0161926 A1 | 7/2007 | Imamura et al. | |
| 2007/0244368 A1 * | 10/2007 | Bayloff | A61B 10/0045 600/300 |
| 2008/0255473 A1 | 10/2008 | Dalebout et al. | |
| 2009/0112125 A1 | 4/2009 | Tamir et al. | |
| 2009/0178459 A1 | 7/2009 | Li et al. | |
| 2009/0197283 A1 | 8/2009 | Gold et al. | |
| 2010/0047914 A1 | 2/2010 | Peyman et al. | |
| 2011/0046453 A1 | 2/2011 | Keil | |
| 2011/0282173 A1 | 11/2011 | Fonduca et al. | |
| 2012/0121643 A1 | 5/2012 | Dubensky et al. | |

FOREIGN PATENT DOCUMENTS

| | | |
|---|---|---|
| WO | 2001/072220 A2 | 10/2001 |
| WO | 2005/103678 A2 | 11/2005 |

* cited by examiner

DEVICE WITH INTEGRATED ALLERGY TESTING

RELATED APPLICATIONS

This application is a continuation of U.S. patent application Ser. No. 13/689,301, filed Nov. 29, 2012, and published as U.S. Patent App. Pub. No. 2014/0187892 on Jul. 3, 2014, which claims the benefit of U.S. Provisional App. No. 61/564,593, filed Nov. 29, 2011, the contents of which are hereby incorporated by this reference in their entirety.

FIELD OF THE DISCLOSURE

The present disclosure generally relates to a medical testing device. More particularly, the present disclosure pertains to a device having an integrated allergy testing system.

BACKGROUND OF THE DISCLOSURE

During surgical procedures and other medical procedures, it is often necessary to determine if a patient has any allergies that may be aggravated during the procedure. Testing for allergies can be a long process. Often, an immediate answer is needed during the procedure.

Extensive use of certain compounds in home and health care products (oral care products, contact lens care products, dressings, ointments, soaps, cosmetics) is causing a larger population to become pre-sensitized to such particular agents. When a pre-sensitized person comes in contact with such an agent, there is a high probability that person could develop much stronger symptoms as severe as anaphylactic shock with cardiac arrest. Currently known tests for such allergies cannot be performed at the patient bedside as they are time consuming, and involve numerous steps and equipment.

It is therefore desirable to provide a device for integrating allergy testing into a medical device.

SUMMARY OF THE DISCLOSURE

The disclosure provides an allergy detection system for use during catheterization. The allergy detection system is incorporated into specialized syringes, connectors for use with standard syringes, or can be an independent test module designed for the sole purpose of allergy detection. The detection system features a test strip, such as an immunochromatographic test strip, and a structure to couple the system to a connector, syringe, or a housing, to form an independent test module. The detection system, by way of test strips, is used to detect potential allergic reactions.

In embodiments, the present disclosure provides a device for testing the presence or absence of a substance in blood, comprising: a coupler or hub that is capable of coupling with a needle, wherein the needle is for withdrawing blood from a subject and for introducing the withdrawn blood into the device; a first chamber for receiving the withdrawn blood; a second chamber configured for holding a test strip; a test strip that is held within the second chamber; a wall or panel that separates the first chamber from the second chamber; at least one aperture in the wall or panel configuring for allowing blood to pass from the first chamber to the second chamber; wherein the second chamber comprises a window for viewing the test strip, wherein the test strip is capable of producing a visible signal that indicates the presence or absence of the substance in the withdrawn blood; and, wherein the window is configured to allow visual detection of the visible signal.

Also provided is the above device, that comprises a syringe and wherein the first chamber is defined by the housing of the syringe. Also provided is the above device, that does not comprise a syringe. Also provided is the above device, that is capable of being coupled to a syringe and to a needle, wherein the device has a hub that is capable of coupling to the hub of the syringe, and wherein the device has a coupler that is capable of coupling to a needle. Moreover, what is provided is the above device, wherein the substance is an antibody. Furthermore, what is contemplated is the above device, wherein the substance is an antibody of the class IgG, IgA, or IgE. Additionally, what is embraced is the above device, wherein the substance is an antibody that specifically binds to an antimicrobial agent, e.g., antiseptic or antibiotic.

In embodiments, what is provided is the above device that is capable of: testing for the presence or absence of a first substance in the blood; and, testing for the presence or absence of a second substance in the blood; wherein the test strip is capable of separately providing a first visual signal for the first substance and a second visual signal for the second substance. Also, what is provided is the above device, wherein the first substance is an IgE antibody that specifically binds latex and the second substance is an IgE antibody that specifically binds an antiseptic. What is further embraced is the above device, wherein the second chamber comprises a flexible dome, and wherein the flexible dome is capable of flexing radially outward; wherein in use the flexible dome flexes radially outwards and creates a partial vacuum that is capable of drawing blood out of the first chamber and into the second chamber; wherein a sliding latch is operably linked with the flexible dome; wherein in use the sliding latch is capable of being slid over the dome to compress the flexible dome radially downwards and increase the pressure within the second chamber; and wherein in use the sliding latch is capable of being slid away from the dome to release the dome and allow the dome to flex radially outwards thereby creating a partial vacuum in the second chamber. Alternatively, the first substance can be an antibody of the IgG, IgA, IgM, or IgD class. Alternatively, the second substance can be an antibody of the IgG, IgA, IgM, or IgD class.

In yet another aspect, what is provided is the above device, further comprising an end-cap, wherein the end-cap is configured for contacting and stabilizing the test strip, and configured for contacting and stabilizing the proximal portion of a needle that is coupled to said device. Also provided is the above device, wherein the second chamber comprises a proximal end and a distal end, and wherein one or both of the proximal end and distal ends comprises an opening for installing the test strip from the second chamber. In yet another aspect, what is provided is the above device, wherein the second chamber comprises a proximal end and a distal end, and wherein one or both of the proximal end and distal ends comprises an opening for installing the test strip from the second chamber, further comprising one or more end caps that capable of capping one or both of the proximal end and the distal end.

What is further embraced, is the above device further comprising a needle, wherein the needle is reversibly coupled to the coupler. Also contemplated is the above device that does not comprise a needle.

In yet another embodiment, what is contemplated is a device for testing the presence or absence of IgE in blood, comprising: a coupler or hub that is capable of coupling with a needle, wherein the needle is for withdrawing blood from a subject and for introducing the withdrawn blood into the device; a first chamber for receiving the withdrawn blood; a second chamber configured for holding a test strip; a test strip that is held within the second chamber; a wall or panel that separates the first chamber from the second chamber; at least one aperture in the wall or panel configuring for allowing blood to pass from the first chamber to the second chamber; wherein the second chamber comprises a window for viewing the test strip; wherein the test strip is capable of producing a visible signal that indicates the presence or absence, in the withdrawn blood, of an antibody of the IgE class that specifically binds to an antiseptic or an antibiotic; and, wherein the window is configured to allow visual detection of the visible signal. Also provided is the above device, wherein the test strip is an immunochromatographic test strip.

In a process embodiment, what is provided is a process for allergy detection during catheterization, comprising: the step of drawing blood from a subject into the first chamber of a device that comprises: (a) a coupler or hub that is capable of coupling with a needle, wherein the needle is for withdrawing blood from a subject and for introducing the withdrawn blood into the device; (b) a first chamber for receiving the withdrawn blood; (c) a second chamber configured for holding a test strip; (d) a test strip that is held within the second chamber; (e) a wall or panel that separates the first chamber from the second chamber; (f) at least one aperture in the wall or panel configuring for allowing blood to pass from the first chamber to the second chamber; (g) wherein the second chamber comprises a window for viewing the test strip, (h) wherein the test strip is capable of producing a visible signal that indicates the presence or absence of the substance in the withdrawn blood; and, (i) wherein the window is configured to allow visual detection of the visible signal; the step of allowing at least some of the drawn blood to enter the second chamber of the device; wherein a needle is coupled to the device; and, wherein in use, at least some of the withdrawn blood enters the needle and then enters the first chamber, then enters the second chamber, and then contacts the test strip.

In yet another process embodiment, what is provided is the above process, further comprising a reaction that is mediated by the test strip, wherein the reaction produces a visual signal that indicates presence or absence of a substance that mediates an allergy. Also provided is the above process, wherein the drawing blood into the first chamber is urged by one or more of: (a) Blood pressure of the subject; (b) Vacuum produced by a syringe plunger of the device; (c) Vacuum produced by a flexible dome of the device; and (d) Capillary action of the test strip of the device. In yet another process embodiment, the disclosure provides the above process wherein the test strip is configured for detecting an antibody that specifically binds an antimicrobial agent, e.g., antiseptic or antibiotic; wherein in use the test strip provides a visual signal that the blood does not contain detectable antibodies that specifically bind to the specific antimicrobial agent, e.g., antiseptic or antibiotic; followed by the step of inserting a catheter into the subject, wherein the catheter is impregnated or coated with the antimicrobial agent, e.g., antiseptic or antibiotic.

Also provided is the above process, wherein the test strip is configured for detecting an antibody that specifically binds an antimicrobial agent, e.g., antiseptic or antibiotic; wherein in use the test strip provides a visual signal that the blood does contain detectable antibodies that specifically bind to the specific antiseptic or antibiotic; followed by the step of making a decision on whether or not to insert a catheter that is impregnated or coated with the antiseptic or antibiotic; and, wherein the decision is to refrain from inserting the catheter in the subject, followed by the step of inserting a catheter into the subject, wherein the catheter is not impregnated or coated with the antiseptic or antibiotic.

In a system embodiment, the disclosure provides a system comprising, in combination, a medical instrument that is capable of holding blood, and a medical device that comprises: (a) a coupler or hub that is capable of coupling with a needle, wherein the needle is for withdrawing blood from a subject and for introducing the withdrawn blood into the device; (b) a first chamber for receiving the withdrawn blood; (c) a second chamber configured for holding a test strip; (d) a test strip that is held within the second chamber; (e) a wall or panel that separates the first chamber from the second chamber; (f) at least one aperture in the wall or panel configuring for allowing blood to pass from the first chamber to the second chamber; (g) wherein the second chamber comprises a window for viewing the test strip, (h) wherein the test strip is capable of producing a visible signal that indicates the presence or absence of the substance in the withdrawn blood; and, (i) wherein the window is configured to allow visual detection of the visible signal. What is also embraced, is the above system, wherein the combination is a reversible combination or a permanent combination. Furthermore, what is provided is the above system, wherein the combination is a reversible combination, wherein the device and the medical instrument are held in combination by one or more of a clip, snap, lock, or tab. Also disclosed, is the above system, wherein the combination is a permanent combination, wherein the device and the medical instrument are held in combination by one or more of an adhesive or integral molding. In yet another system embodiment, what is provided is the above system, wherein the medical instrument comprises one or more of a syringe, trocar, catheter, introducer, sheath, hub, pump, or valve.

The foregoing needs are met, to a great extent, by the present disclosure, wherein in some embodiments a device with an integrated allergy testing system that is capable of overcoming the disadvantages described herein at least to some extent is provided.

In accordance with an embodiment of the present disclosure an allergy testing device for testing a sample includes a housing having a proximal end and a distal end. The housing can also include an outer wall defining an inner chamber extending through at least a portion of the housing. The device can also include a needle extending from a distal end of the housing. Additionally, the device can include an immunochromatographic test strip configured to indicate whether a predetermined antibody is present in the sample. The test strip can be positioned in the housing.

In accordance with another embodiment of the present disclosure, a syringe with an integrated allergy testing system includes a syringe housing having an outer wall defining an inner chamber extending through at least a portion of the syringe housing and the syringe housing having a proximal end and a distal end. The syringe can also include a needle extending from a distal end of the housing. Additionally a syringe plunger can be movably disposed within the inner chamber of the syringe housing. The syringe can also include an immunochromatographic test component configured to indicate whether a predetermined antibody is present in a sample, where the sample can be aspirated into the syringe, and wherein the test component is positioned in the syringe housing.

In accordance with another embodiment of the present disclosure, an attachment for a medical device having an integrated allergy testing system can include a housing having a proximal end and a distal end, wherein the proximal end is configured to couple to a medical device and the distal end is configured to receive a needle. The attachment can also include an immunochromatographic test component configured to indicate whether a predetermined antibody is present in a sample, wherein the test component is positioned in the housing. The sample can be aspirated into the housing. Additionally, the attachment can include a window disposed in the housing such that the test component is viewable.

There has thus been outlined, rather broadly, certain embodiments of the invention in order that the detailed description thereof, herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

Components for the methods and devices of the disclosure are available, for example, from any major medical device company, for example, Medtronic of Minneapolis, Minn.; Advanced Cardiovascular Systems in Santa Clara, Calif.; Baxter International of Deerfield, Ill.; Abbott Laboratories at Abbott Park, Ill., Edwards Lifesciences, Irvine, Calif., and Boston Scientific of Natick, Mass. Components of the present disclosure can be made, without limitation, by molding, blow molding, slush molding, injection molding, rotational molding, compression molding, extrusion, thermoforming, stamping, calendaring, and so on (Brazel, C S; Rosen, S L (2012) Fundamental Principles of Polymeric Materials. Wiley, Hoboken, N.J.).

BRIEF DESCRIPTIONS OF THE DRAWINGS

DETAILED DESCRIPTION

Figure 1:
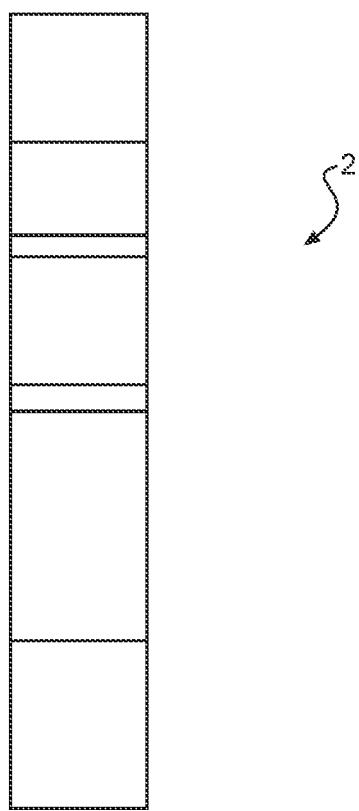
FIG. 1 illustrates a test strip in accordance with an embodiment of the invention.

The present disclosure provides in some embodiments, an allergy detection system for integration into medical devices. For instance, in accordance with embodiments of this invention, the allergy detection system can be incorporated into a specialized syringe, a connector for use with a standard syringe, or an independent test module, designed for the sole purpose of allergy detection. The detection system can include, without limitation, an immunochromatographic membrane and structure to couple it to a connector or syringe or a housing to form an independent test module. The detection system can be used to detect any potential allergies that can be identified using immunochromatography.

In embodiments, what is provided is a device and related methods for point of care testing. For example, where a needle is introduced for use in the Seldinger technique, the needle can be used in conjunction with device and method of the present disclosure for detecting antibodies and predicting adverse allergic reactions. The Seldinger technique, includes the initial step of inserting a needle into a patient's blood vessel, where the Seldinger technique concludes with replacing the needle with a catheter or other medical device. The end-result is that the catheter or other medical device is situated in a subject's blood vessel or other body cavity. The Seldinger technique, and variations thereof, and devices used to perform this technique, are described in Seldinger (1953) Acta Radiologica 39:368-376; U.S. Pat. No. 7,722,567 issued to Tal, U.S. Pat. No. 7,972,307 issued to Kraus, et al, and U.S. Pat. No. 7,938,806 issued to Fisher, et al, which are incorporated by reference. Following testing by device and method of the present disclosure, and where the test gives a negative result (indicating that the subject is not allergic), the clinician can proceed with the Seldinger technique, and replace the needle with a catheter that contains the antigenic drug, antigenic antiseptic, antigenic adhesive, or antigenic latex. Alternatively, if the test gives a positive result and indicates that the subject is likely to be allergic to the antigenic drug, antigenic antimicrobial agent, antigenic antiseptic, antigenic adhesive, or antigenic latex, then the clinician refrains from using the medical device. Where the test gives a positive result, the clinician can use an alternative medical device that does not contain the offending drug, antiseptic, adhesive, or latex, and the like.

In this way, the device and procedure of the present disclosure is used at the point of care, and is integrated into the procedure for using any medical device of interest, and where the device and procedure of the present disclosure can give the clinician a yes/no answer. The device of the present disclosure can be a physical part of a device used for the medical procedure of interest, for example, the device can be connected to a syringe that is used in the Seldinger technique or other procedure. This connection can be by way of a luer lock, Storz lock, or other coupler. Alternatively, the device of the present procedure can be integrated into a syringe that is, permanently molded into the syringe that is used in the Seldinger technique or other procedure.

In exclusionary embodiments, the present disclosure includes only test-strip devices that are integrated into a syringe. In another exclusionary embodiment, the present disclosure excludes test-strip devices that are not integrated into a syringe. In exclusionary embodiments, the present disclosure includes only test-strip devices that are integrated into a needle hub, trocar, dilator, syringe, syringe barrel, introducer, and the like. In another exclusionary embodiment, the present disclosure excludes test-strip devices that are not integrated into a needle hub, that are not integrated into a trocar, that are not integrated into a dilator, that are not integrated into a syringe or syringe barrel, that are not integrated into an introducer, and the like.

Immune Disorders Arising from Exposure to Medical Devices and Pharmaceuticals

In embodiments, the present disclosure provides a device and related methods, for detecting antibodies against components of medical devices or components of pharmaceuticals, and for quantitating or for predicting allergic reactions in a subject to be exposed to the medical device or the pharmaceutical. What can be quantitated is, for example, antibodies of one or more of the classes IgG, IgA, IgM, IgD, or IgE, that are present in a subject's bloodstream or in any biological fluid. The device and related methods are configured for quantifying or for predicting anaphylactic-type reactions or bronchospasm (Layton et al (1989) Clin. Exp. Allergy. 19:307-314; Terazawa et al (1998) Anesthesiology. 89:1298-1300), allergic contact dermatitis, irritant contact dermatitis, photoallergic contact dermatitis, or immediate type contact reactions (Kutzscher (2012) Clin. J. Oncol. Nurs. 16:E48-55; Krasteva (1999) Eur. J. Dermatol. 9:144-159), arising from exposure to an antimicrobial agent or an antiseptic, e.g., a biguanide antiseptic.

Allergic Reactions Against and Antibodies to Antimicrobial Agents, and to Other Components of Medical Devices Device and methods of the present disclosure can detect antibodies, present in a subject's blood, serum, or other biological fluid, where the antibodies specifically bind to an antimicrobial agent, such as an antiseptic or antibiotic (Torres et al (2009) 19:67-68), antibiotics such as rifampicin (Feng et al (2011) Eur. J. Dermatol. 21:696-699), adhesives on catheters (Meikle et al (2012) Can. J. Anaesth. 59:815-816), thimerosol or other preservatives in medical devices (Ancona et al (1990) Dermatol. Clin. 8:95-105). Allergic reactions to latex, and antibodies against latex, have been described (Patriarca et al (2002) J. Investig. Allergol. Clin. Immunol. 12:169-176; Unsel et al (2012) Int. Arch. Allergy Immunol. 158:281-287). Allergic reactions (analphylaxis) can occur in response to medical devices impregnated with one or more antiseptics (Darouiche and Raad (1999) New Engl. J. Med. 1762 (1 page)). Antibodies of the classes IgG and IgA are associated with drug-induced eruptions (pemphigus folicaeus) (Feng et al (2011) Eur. J. Dermatol. 21:696-699). Antibodies of the classes IgG and IgE are associated with allergic reactions to antiseptics (Layton et al (1987) Mol. Immunol. 24:133-141). Antibodies of the IgE class have been identified that are responsible for hypersensitivity to various beta-lactam antibiotics (Gunez et al (2012) J. Investig. Allergol. Clin. Immunol. 22:41-47). IgE antibodies have also been identified that specifically react against latex (Galindo et al (2011) J. Investig. Allergol. Clin. Immunol. 21:459-465).

The term "antimicrobial" encompasses, but is not limited to, antiseptics and antibiotics.

Detecting Antibodies and Other Molecules that can Provoke Adverse Events

Antibodies in blood or in other biological fluids can be detected, for example, by way of reagents in a test strip. The reagents can be covalently or non-covalently attached to the surface of a test strip, the reagents can be adsorbed to a test strip, the reagents can be absorbed to a test strip, the reagents can be covalently or non-covalently bound to interior of test strip, such as porous interior or fibrous interior, or any combination of the above. Reagents, test strips, substrates, for immune assays, including color reactions, and the like, are provided, for example, from U.S. Pat. No. 7,544,324 issued to Tung et al, U.S. Pat. No. 7,438,852 issued to Tung et al, U.S. Pat. No. 7,989,217 issued to Yee et al, U.S. U.S. Pat. No. 7,910,381 of Ford et al, each of which is individually incorporated herein by reference, each in its entirety. The present disclosure encompasses detection of antibodies, such as IgG, IgA, IgM, IgD, or IgE, detecting B cells that express IgE or other classes of antibodies, by way of test strip technology. Several antibody classes can be simultaneously expressed in the body, and that recognize the same antigen. Accordingly, the present disclosure provides a test strip that can detect antibodies two or more of the classes IgG, IgA, IgM, IgA, IgD, or IgE. In one embodiment, the test strip detects two different classes, and provides two different colors. In another embodiment, the test strip detects two different classes, and provides the same color for both of the respective color reactions, but at different locations in the test strip. In yet another embodiment, the test strip detects a plurality of different antibody classes (or detects a plurality of different specific antibodies that bind to respective different antigens, where all of these specific antibodies are in one particular class). Combinations of the previous embodiments are also provided, e.g., detecting IgG that binds to an antibiotic, and detecting IgE that binds to latex, or detecting an antibody that binds to an antimicrobial and an antibody that binds to a pathogen. Color reaction can be provided by a label that comprises a metal, a colloidal particle such as colloidal gold, a dye particle, or results from a reaction catalyzed by peroxidase or alkaline phosphatase (see U.S. Pat. No. 7,262,019 issued to Kovalenko, U.S. Pat. No. 5,200,312 issued to Oprandy, U.S. Pat. No. 5,637,468 issued to Mason, and U.S. Pat. No. 6,503,726 issued to Anne, which are each incorporated herein in their entirety). Where a gold labeled anti-IgE antibody is used, for example, a test sample (e.g., blood) reacts with the gold labeled anti-IgE antibody, forming a complex. The complex travels across a membrane where immobilized allergens capture the complex, resulting in a colored line (see U.S. Pat. No. 7,629,127 issued to Hubscher, which is incorporated herein by reference).

The following provides a non-limiting example. For detection of anti-antiseptic antibodies, blood can be deposited at a sample receiving area located at a first end of the test strip. Flow of solvent from the first end of the test strip towards the opposite end of the test strip draws any antibodies towards the test strip, and draws the antibodies over a region of the test strip that contains conjugates of gold-antiseptic. When the antibodies migrate over the area that contains gold-antiseptic, the result is an insoluble complex that forms a visually detectable line. Conjugates of gold-antiseptic that are not trapped as part of this insoluble complex continue to migrate on the test strip, and do not contribute to the visual signal of the line. As an alternative to using a conjugate of gold-antiseptic, what can be used is a conjugate of gold with an antibody that specifically binds to anti-antiseptic antibodies (anti-idiotype antibodies). The above narrative applies to anti-antiseptic antibodies, but also to embodiments where the antigen is an antibiotic, a pharmaceutical, a drug, latex, an adhesive, and the like.

In a non-limiting embodiment, what is provided is a device that encompasses an immunoassay with all reagents embedded on a test strip that performs without the use of instruments. Total IgE in a biological fluid is bound by anti-human IgE immobilized on test strips in the IgE reactive field of the test strip. Visualization of captured IgE is indicated by colloidal gold labeled anti-human IgE. Excess labeled antibodies are captured by antibodies in the control field. A control line appears in the control field and determines when enough of the biological fluid has been collected. The presence of IgE in the sample is visualized by the appearance of a dark-colored line, e.g., a red line, in the reactive field and the control field. Absence of a line in the control field, regardless of the presence of line in the reactive field, indicates an invalid assay result. The area on the support identifying the reactive field and control field are on the back surface of the support in two colors. A sample with IgE in the normal reference range lacks a line in the reactive field but has a line in the control field. The presence of lines in the reactive and control fields indicates a sample with elevated total IgE levels. The device provides a qualitative/semi-quantitative measure of total IgE in the biological fluid when the intensity of color on the test strip is visually observed. The skilled artisan can divide or classify the different intensities of signal as negative or as positive, and the skilled artisan can prepare a standard operating procedure (SOP) that sets forth these different intensities. What is also provided is the above embodiment, but where it applies to other antibody classes, e.g., IgG, IgA, IgM, or IgD.

In a non-limiting embodiment, what is provided is a device that comprises a series of capillary beds (elements), for example, made of cellulose. The first element (a sample pad) acts as a sponge and can hold an excessive amount of biological fluid. Then, the fluid migrates to the second element (conjugate pad). The second element is manufactured with a conjugate, a dried format of particles in a soluble matrix that contains reagents that promote the desired chemical reaction between the target molecule (antigen) and its binding partner (antibody) that has been immobilized on the surface of the particle. At the time that the sample fluid dissolves the soluble matrix, it also dissolves the particles and the sample and conjugate mix while flowing through the porous structure. In this way, the analyte binds to the particles while migrating further through the third capillary bed. This material has one or more regions or stripes where a third molecule has been immobilized. By the time the sample-conjugate mix has migrated to these stripes, analyte has been bound on the particle and the third capture molecule binds the complex. When additional fluid passes the stripes, particles accumulate and the stripe-area changes color. In embodiments, there can be two stripes: one (the control) that captures any particle and demonstrates that reaction is in working order, the second contains a specific capture molecule and only captures those particles on which an analyte molecule has been immobilized.

Duration of Detection

In embodiments, what is provided is a device that is capable of detecting an antibody responsible for an allergic reaction, for example, to an antibiotic or antiseptic,
(1) During a blood draw that is dedicated to this detection;
(2) Only during a blood draw that is dedicated to this detection, with no capability during subsequent procedures, e.g., during insertion of a catheter or other medical instrument. This is an exclusionary embodiment;
(3) During a period of time when a catheter or other medical instrument is indwelling in a subject, that is, when a catheter or other medical instrument is operably linked to a subject. This period of time can be, e.g., at least ten minutes, at least one hour, at least one day, at least one week, at least one month, and the like;
(4) Only during a period of time when a catheter or other medical instrument is indwelling in a subject, but not capable of detecting the antibody during a blood draw that is solely dedicated to the detection of the antibody. This is an exclusionary embodiment.

Antibodies and Other Reagents

"Specifically" or "selectively" binds, when referring to a ligand/receptor, nucleic acid/complementary nucleic acid, antibody/antigen, or other binding pair (e.g., a cytokine to a cytokine receptor) indicates a binding reaction which is determinative of the presence of the protein in a heterogeneous population of proteins and other biologics. Thus, under designated conditions, a specified ligand binds to a particular receptor and does not bind in a significant amount to other proteins present in the sample. Specific binding can also mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, conventionally at least ten times greater, more normally at least 20-times greater, more typically at least 100-times greater, and most typically at least 1000-fold than the affinity with any other binding compound (see, e.g., US 2012/0121643 of Dubensky, which is incorporated by reference).

In a typical embodiment an antibody will have an affinity that is greater than about $10^9$ liters/mol, as determined, e.g., by Scatchard analysis (Munsen, et al. (1980) Analyt. Biochem. 107:220-239). It is recognized by the skilled artisan that some binding compounds can specifically bind to more than one target, e.g., an antibody specifically binds to its antigen, binds to lectins by way of the antibody's oligosaccharide, and also binds to an Fc receptor by way of the antibody's Fc region.

In embodiments, the disclosure provides test strip that is capable of detecting antibodies in blood, where the antibodies specifically bind to a pathogen. Anti-pathogen antibodies have been characterized. Reagents and kits are available for detecting antibodies that specifically bind to viruses (e.g., HIV, HCV, HBV), fungi, and bacteria (see, e.g., Novack et al (2006) J. Clin. Microbiol. 44:2909-2913; Hennessey et al (2009) J. Urban Health. 86:93-105; Thurman et al (2009) Clin. Infect. Dis. 48:1244-1249; Alexander et al (1996) J. Clin. Microbiol. 34:1180-1183).

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

A composition that is "labeled" is detectable, either directly or indirectly, by spectroscopic, photochemical, biochemical, immunochemical, isotopic, or chemical methods. For example, useful labels include $^{32}P$, $^{33}P$, $^{35}S$, $^{14}C$, $^{3}H$, $^{125}I$, stable isotopes, epitope tags fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

DETAILED DESCRIPTIONS OF THE FIGURES

The invention will now be described with reference to the drawing figures, in which like reference numerals refer to like parts throughout. As illustrated in FIG. 1, the allergy detection system can include an immunochromatographic membrane 2 (PVDF or nitrocellulose material) in strip or cassette format that can detect elevated levels of an allergen by employing a highly sensitive detecting antibody and a carrier-protein conjugated hapten. The antibody is labeled with a signal generator (e.g., colloidal gold), which is placed in the dry state at a predetermined site on the membrane. Using this novel approach the clinician (catheter inserters) would be able to determine if a patient is at risk of developing an allergic reaction before potentially introducing an allergen into a patient's system. The system also provides ease of use to the hospital staff as it does not require any additional step, equipment or time other than what is needed for standard procedures.

Figure 2:
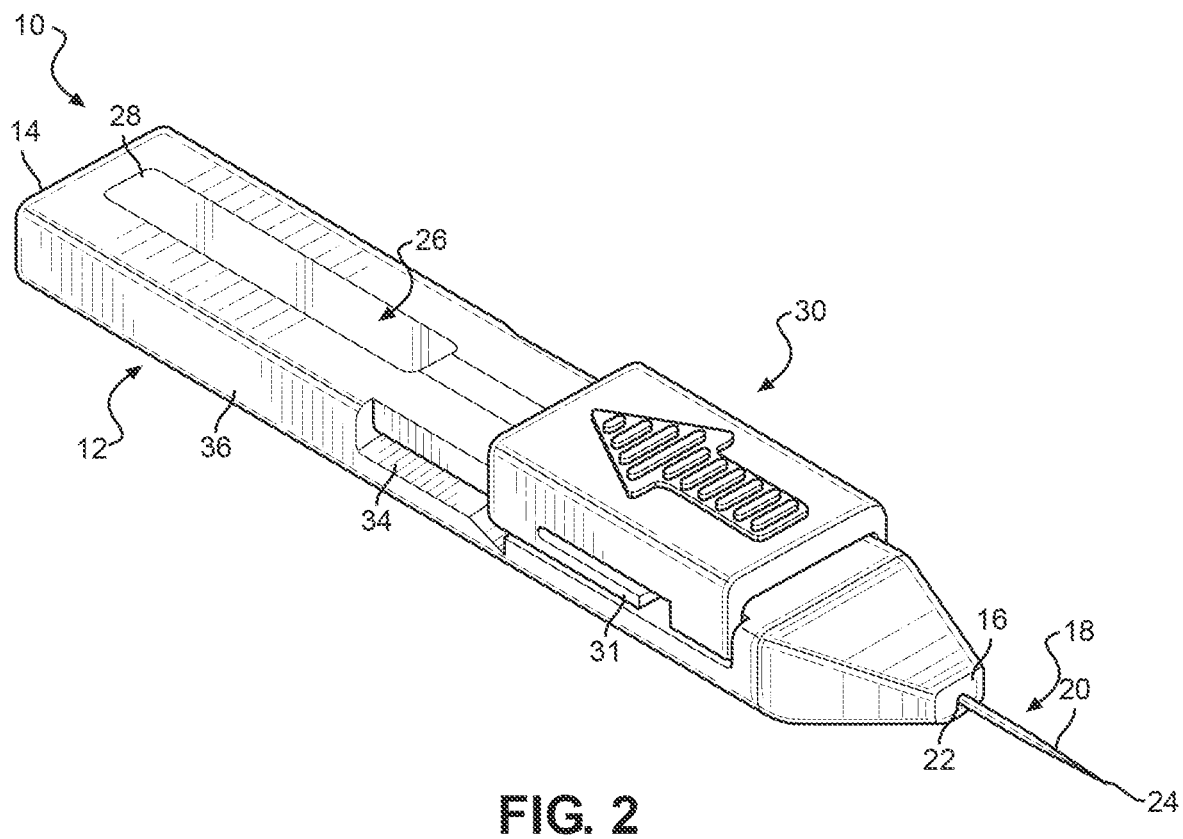
FIGS. 2 and 3 illustrate a perspective view of an independent allergy testing module in accordance with an embodiment of the invention.
Figure 3:
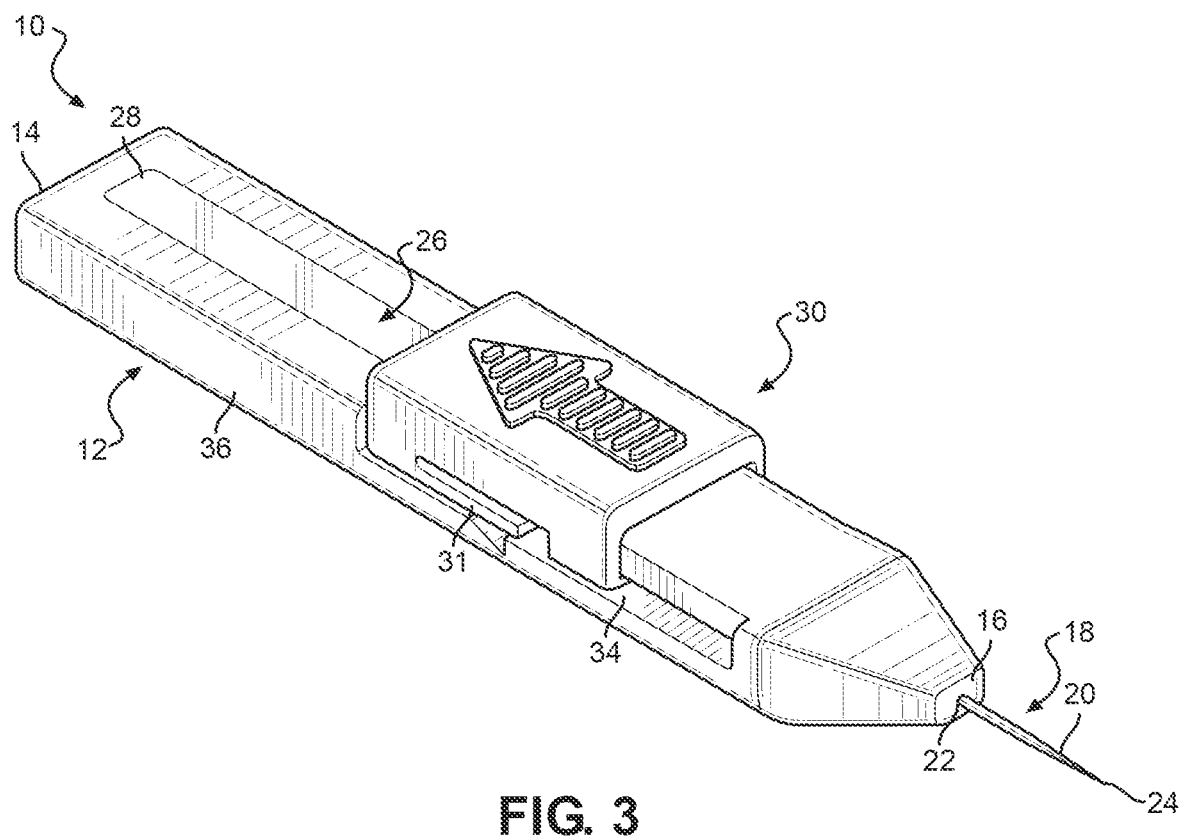
Figure 4:
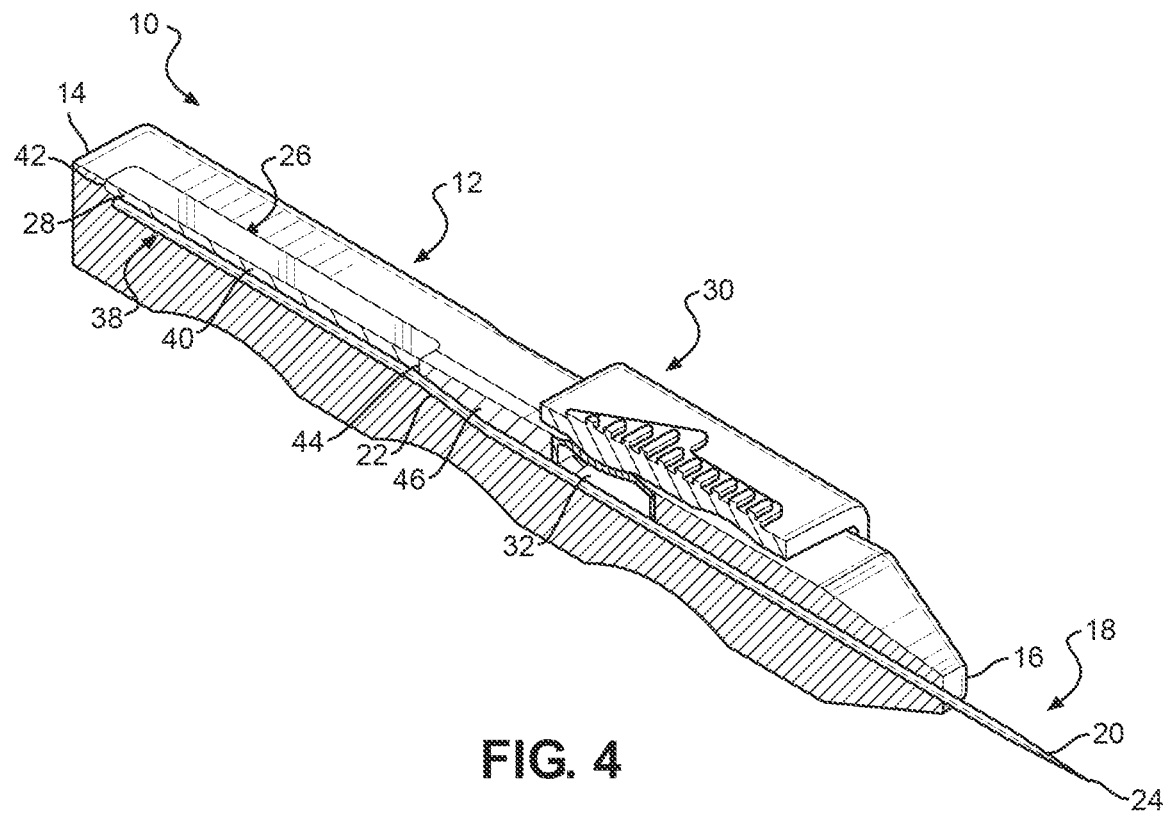
FIGS. 4 and 5 illustrate a sectional view of the independent allergy testing module illustrated in FIGS. 2 and 3 in accordance with an embodiment of the invention.
Figure 5:
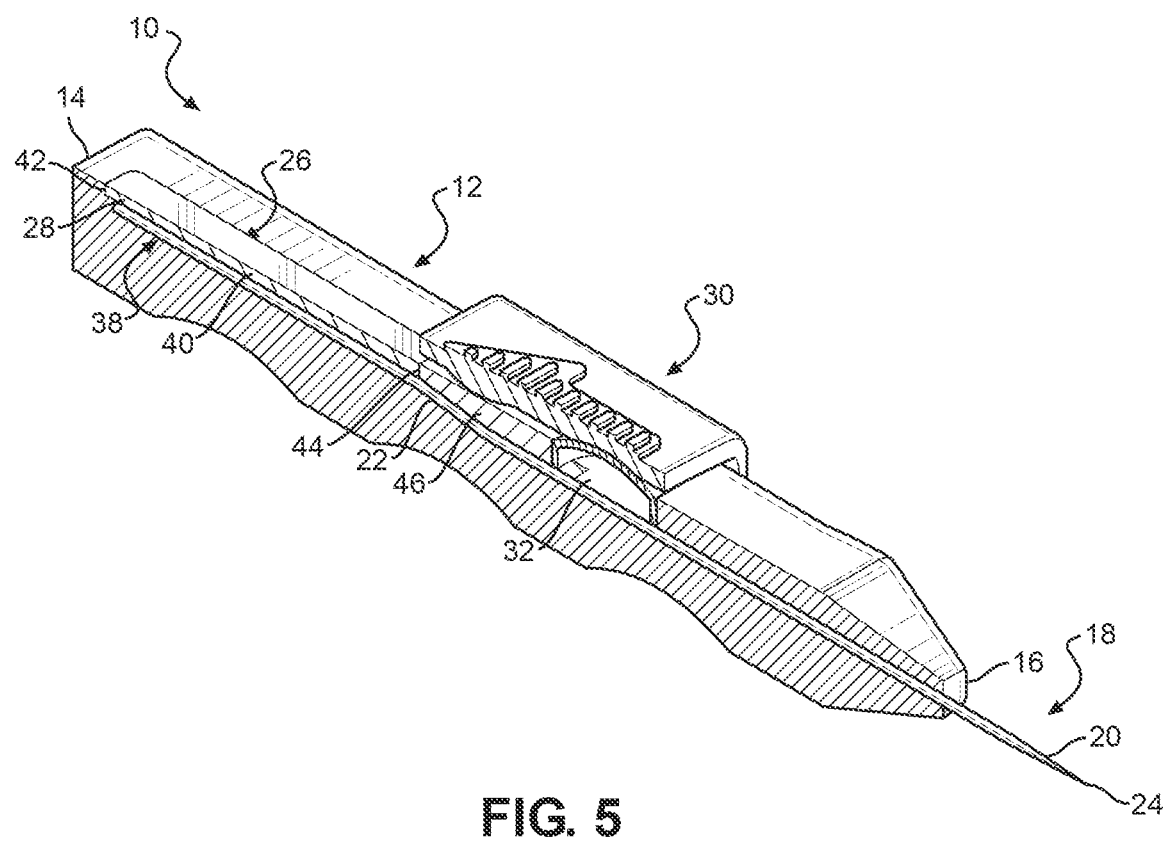
Figure 6:
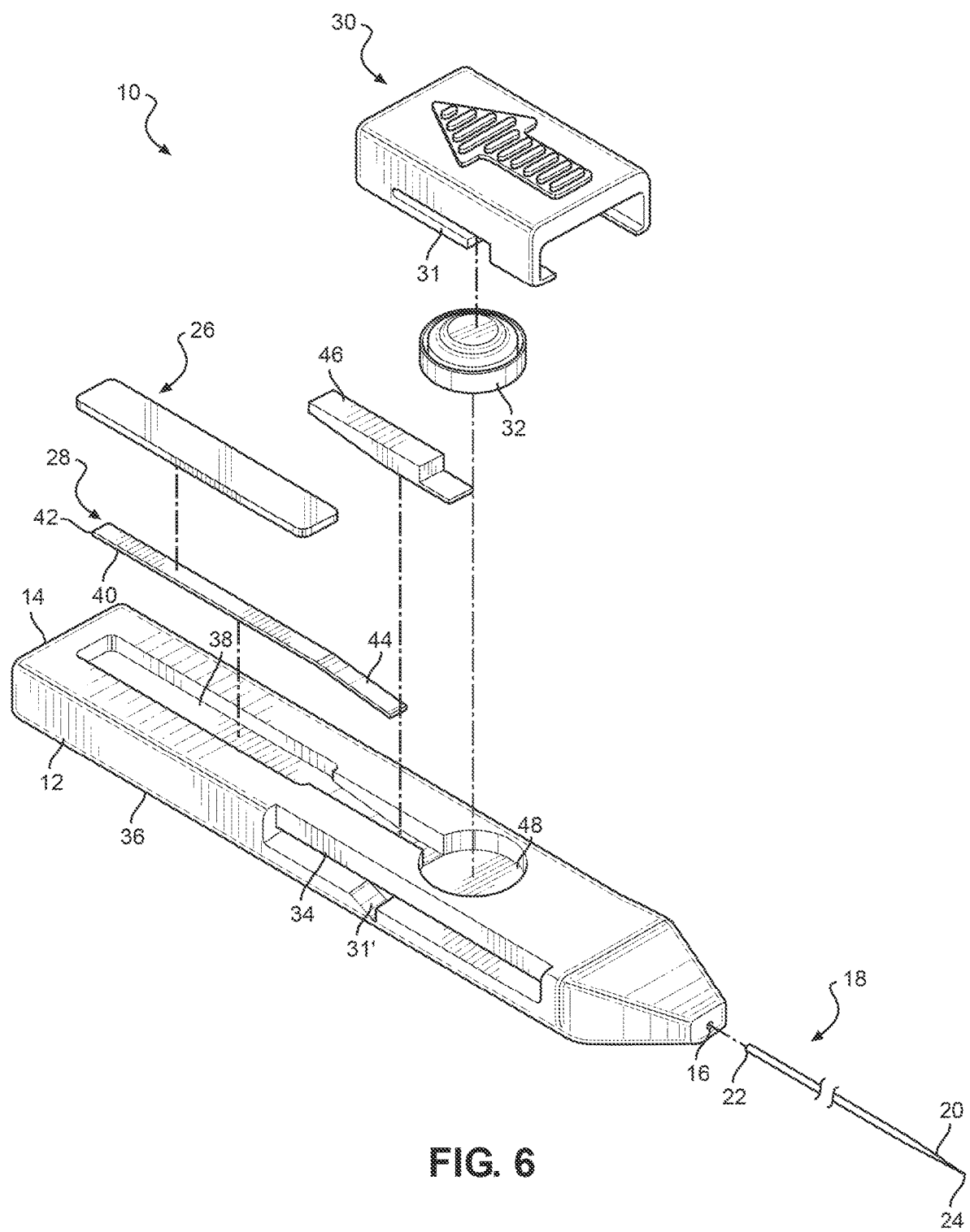
FIG. 6 illustrates an exploded view of the independent allergy testing module illustrated in FIGS. 2-5 in accordance with an embodiment of the invention.

FIGS. 2 and 3 illustrate an independent testing module in accordance with an embodiment of this invention. FIG. 2 illustrates the independent testing module 10 in its inactive state and FIG. 3 illustrates the independent testing module 10 in its active state. The independent testing module 10 includes a housing 12 having a proximal end 14 and a distal end 16. A needle 18 can extend from the distal end 16 of the housing 12. The needle 18 can include a sharpened distal end 20 and a proximal end 22 that extends into the housing 12. The needle 18 can be generally configured as a hypodermic-type needle with a bore 24 extending through its length. The testing module 10 can also include a viewing window 26, through which test strip 28 can be observed. The test strip 28 is disposed within the housing 12 behind the window 26, such that the operator can view any changes in the strip 28 during use. The testing module 10 can also include a slide 30 and a vacuum button 32 (as illustrated in FIGS. 4-6). In the inactive state illustrated in FIG. 2, the slide 30 is positioned toward the distal end of the testing module 10. When the needle 18 is inserted into the patient and testing is required the slide 30 can be moved from its distal, forward position to a proximal position. Slot 34, positioned on a side 36 of housing 12 in FIGS. 2 and 3, is configured to lock the slide 30 into place after it has been activated into the proximal position.

The button can comprise an elastic material, for example, silicone, latex, or polyurethane. In one non-limiting embodiment, button is thinner at the peak of the button's dome, and is thicker at the base of the dome.

FIGS. 4 and 5 illustrate a sectional view of the independent testing module 10 illustrated in FIGS. 2 and 3. FIG. 4 is a sectional view of the independent testing module 10 in the inactive position, as illustrated in FIG. 2, and FIG. 5 is a sectional view of the independent testing module 10 in the active position, as illustrated in FIG. 3. The housing 12 can define an inner space 38 near the proximal end 14 of the testing module 10. The test strip 28 can be disposed in this inner space 38. In addition, an absorbent pad 40 can be integrated into the bottom of the test strip 28 in this inner space 38. The test strip 28 can include a proximal end 42 and a distal end 44. Cap 46 is positioned on top of the junction between the proximal end of the needle 22 and the distal end 44 of the test strip 28.

The following concerns non-limiting embodiments of cap (46). The cap holds or positions the test strip. The cap holds or positions the proximal end of the needle. Also, the cap creates or defines small vacuum pathways from the vacuum button to the proximal end of the needle. In a preferred embodiment, the cap (46) is not removable.

In a non-limiting embodiment of the present disclosure, the absorbent pad is an integrated part of the test strip. In another non-limiting embodiment, the absorbent pad is separate from, and does not occupy the same space as, the test strip. The absorbent pad increases the total volume of sample that enters the test strip. The absorbent pad can block the migration of blood cells, and thereby provide a clean field for development and detection (by clinician's eyes) of the color reaction. In addition, or alternatively, the absorbent pad can draw the biological fluid by way of capillary attraction, resulting in wetting of a broad area of the test strip. In another embodiment, the device comprises only a test strip and does not contain any absorbent pad. In one embodiment that does not contain an absorbent pad, the test strip does not disperse fluid by way of capillary attraction, and the biological fluid is sufficiently dispersed without capillary attraction. In another embodiment, the test strip is sufficiently thick (or thin but sufficiently opaque) that it blocks passage of red blood cells to the viewable area where the color reaction takes place. In yet another embodiment, the test strip has capillary attraction and is also sufficiently thick (or thin but sufficiently opaque) to block passage of red blood cells, and to prevent the red blood cells from residing in the viewable area where the color reaction takes place). Absorbent pad can comprise cellulose, polyvinylidene fluoride (PVDF), nitrocellulose, and the like. Filter material suitable as a matrix for test strips, and for serving as a reaction area for color reagents, and optionally for blocking red blood cells, and optionally for serving as a capillary attractant for attracting and dispersing a biological fluid, are available (EMD Millipore, Darmstadt, Germany; Millipore, Billerica, Mass.; Membrane Solutions, Plano, Tex.). U.S. Pat. No. 4,855,240 of Rosenstein, U.S. Pat. No. 4,703,017 of Campbell, and U.S. Pat. No. 4,376,110 of David et al, disclose absorbent materials, capillary materials, test strips, labels, and immunoassays, are incorporated herein by reference in their entirety.

FIGS. 4 and 5 also illustrate a vacuum button 32 of the independent testing module 10. In the inactivated position illustrated in FIG. 4, the vacuum button 32 is depressed by slide 30. This keeps the vacuum button 32 depressed until the needle 18 is inserted and ready to extract blood. As illustrated in FIG. 5, once the device is in position, the slide 30 is retracted to the active position, releasing vacuum button 32, thus creating a vacuum and allowing blood to flow into the bore 24 of the needle 18. Locking the slide 30 in the active position prevents depression of the vacuum button 32, when the needle 18 is inserted into a vein of the patient, in turn preventing air from potentially being pushed into the access point or blood being squirted from the device after it has been used. The blood aspirated into the testing module 10 is absorbed from the bottom end of the testing strip 28. The absorbent pad 40 can absorb the plasma sample after the completion of the signal detection reaction. The absorbent pad 40 can also include a porous backing and an absorbent dispersed, adsorbed, or coated into the pores of the porous backing. A color signal can appear within approximately 10 minutes within the viewing window 26, but could take less time or more time depending on the detecting antibodies contained in the test strip.

FIG. 6 illustrates an exploded view of the independent testing module 10 as shown in FIGS. 2-5. As shown in FIG. 6, the testing module includes the housing 12 and a needle 18 coupled to a distal end 16 of the housing 12. The housing 12 also defines the inner space 38 near the proximal end 14 of the testing module 10. The test strip 28 can be disposed in this inner space 38. In addition, an absorbent pad 40 can be integrated into the test strip 28 in this inner space 38. The test strip 28 can include a proximal end 42 and a distal end 44. Cap 46 is positioned on top of the junction between the proximal end of the needle 22 and the distal end 44 of the absorbent pad 40. FIG. 6 also illustrates the slide 30 and the vacuum button 32 which work together to release the vacuum for the independent testing module such that it can aspirate the blood sample. The slide 30 and vacuum button 32 also prevent the vacuum button from being re-depressed to prevent pushing any air into the entry site or allowing any blood to spurt out after use. The vacuum button 32 sits within an opening 48 defined by the housing 12. The slide 30 can lock into position via the slot 34, also illustrated in FIGS. 2 and 3. As illustrated, tab 31 interacts with a notch 31' in the architecture of slot 34 in order to lock the slide 30 into place. However, any suitable means of locking the slide into place can be used. Locking the slide 30 in the active position prevents depression of the vacuum button 32, when the needle 18 is inserted into a vein of the patient, in turn preventing air from potentially being pushed into the access point or blood being squirted from the device after it has been used. Cap 46 is also shown and is placed over the junction between the testing strip 28 and the proximal end 22 of the needle 18.

Figure 7:
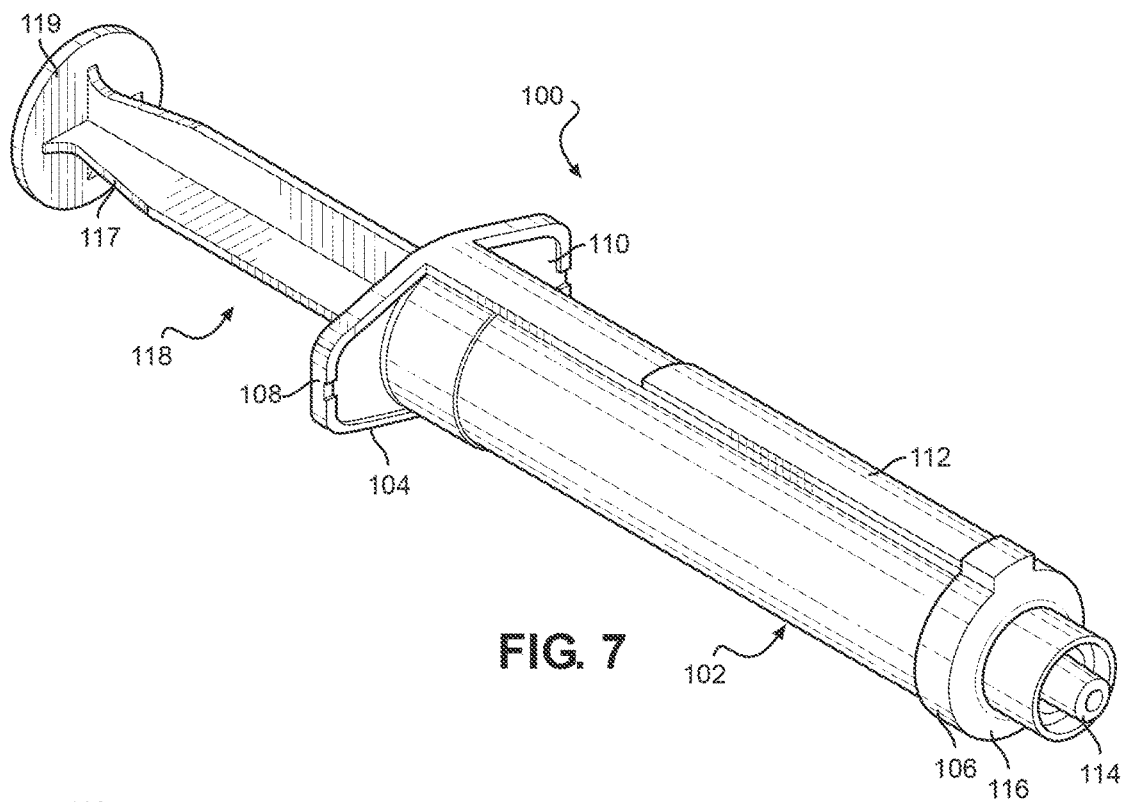
FIG. 7 illustrates a syringe with integrated allergy testing in accordance with an embodiment of the invention.

FIG. 7 illustrates a syringe with integrated allergy testing, in accordance with another embodiment of the integrated allergy testing system. As shown in FIG. 7, the syringe 100 includes a housing 102 having a proximal end 104 and a distal end 106. The proximal end 104 of the housing 102 can include flanges 108, 110 which can serve as finger rests during use of the syringe 100. The housing 102 can include a window 112 positioned such that test strip positioned below the window is visible to a user of the syringe 100. The test strip resides within its own lumen or channel, such that only the distal end of the test strip is exposed to the blood that is aspirated within the syringe housing 102. A needle hub 114 can be positioned at the distal end 106 of the housing 102 and can be configured to couple to a hypodermic-type needle for aspirating blood into a lumen of the syringe 100. A syringe housing cap 116 can be coupled to the distal end 106 to hold the test strip in the housing 102. The syringe 100 can also include a plunger 118 extending into the lumen of the housing 102 for creating negative pressure to aspirate blood into the lumen of the syringe. The plunger 118 can include a thumb rest 119 positioned at a proximal end 117 of the plunger 118.

In embodiments, where test strip resides in its own lumen or channel, blood or other biological sample enters channel through a hole, slit, passage, or crevice, that is about 5% the distal-to-proximal length of the channel, about 10% the distal-to-proximal length of the channel, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, or longer, than the distal-to-proximal length of the channel. Where the slit or crevice is about 100% the distal-to-proximal length of the channel, the result is that blood entering the syringe, or entering a corresponding structure in the module (10), contacts that entire test strip essentially simultaneously.

Regarding the orientation of the channel with respect to the hole, slit, passage, or crevice, the hole, slit, or crevice, can start at a point corresponding to the distal-most portion of the channel, and then migrate proximally. Alternatively, the hole, slit, or crevice, can start at a point corresponding to the proximal-most portion of the channel, and then migrate distally. In yet another alternative, the hole, slit, passage, or crevice, can be situated entirely between the distal-most and proximal-most portions of the channel. For example, the hole or passage can be situated near the half-way point of the channel, where blood entering the hole migrates both in the proximal and in the distal directions.

In embodiments where the hole, slit, passage, or crevice, is about 5% the distal-to-proximal length of the channel, it may be the case that only about 5% of the test strip is wetted by the blood or other biological sample. Alternatively, in embodiments where the hole, silt, passage, or crevice, is about 5% the distal-to-proximal length of the channel, it may be the case that greater than about 5% of the test strip is wetted by the blood or other biological sample, where this greater than amount results from migration of the biological sample through the test strip. Migration can by via diffusion, capillary force, or by a combination of diffusion and capillary force. The above narrative also applies to configurations where the hole, slit, passage, or crevice, is less than 90%, less than 80%, less than 70%, less than 60%, less than 50%, less than 40%, less than 30%, less than 20%, less than 10%, less than 5%, of the length of the distal-to-proximal length of the channel.

Figure 8:
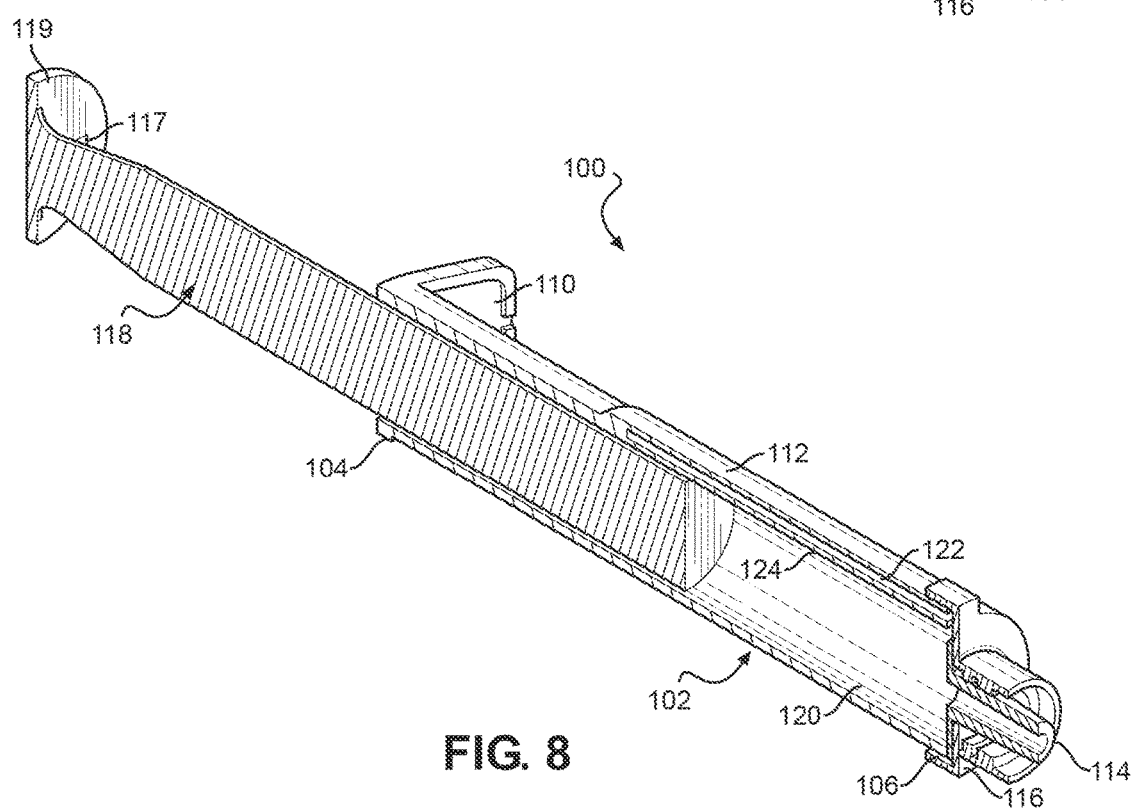
FIG. 8 illustrates a sectional view of the syringe with integrated allergy testing illustrated in FIG. 7 in accordance with an embodiment of the invention.

FIG. 8 illustrates a sectional view of the syringe illustrated in FIG. 7. As shown in FIG. 8, the syringe 100 includes the housing 102 defining a lumen 120, extending therethrough. The plunger 118 is shown extending into the lumen 120 of the housing 102. Additionally, FIG. 8 illustrates test strip 122 positioned within the housing 102 beneath window 112. The syringe housing cap 116 holds the test strip 122 in place beneath the window 112 for observation by the practitioner. Alternately, the test strip 122 can take the form of a cassette or any other appropriate form for positioning within the syringe 100. In addition, an absorbent pad 124 can be integrated into the test strip 122. The absorbent pad 124 can absorb the plasma sample after the completion of the signal detection reaction. The absorbent pad 124 can also include a porous backing and an absorbent dispersed, adsorbed, or coated into the pores of the porous backing. A color signal can appear within approximately 10 minutes within the viewing window 112, but could take less time or more time depending on the antibodies contained in the test strip.

Figure 9:
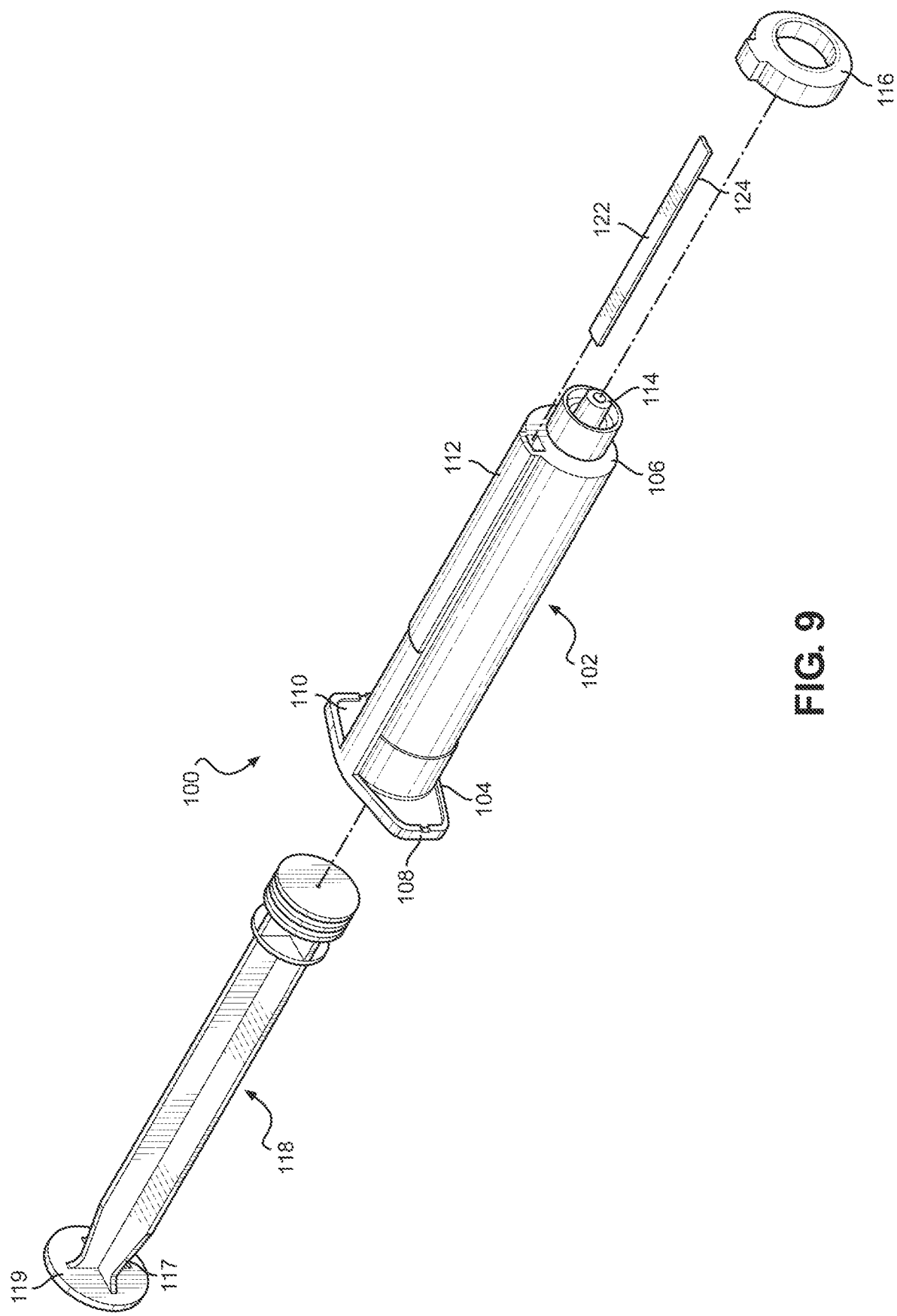
FIG. 9 illustrates an exploded view of the syringe with integrated allergy testing illustrated in FIGS. 7 and 8 in accordance with an embodiment of the invention.

FIG. 9 illustrates an exploded view of the syringe illustrated in FIGS. 7 and 8. FIG. 9 shows the housing 102 having a window 112 for the test strip 122. The syringe housing cap 116 can be used to hold the test strip in place, such that it does not move during testing. The plunger 118 can be configured to slide within the lumen 120 of the housing 112.

Figure 10:
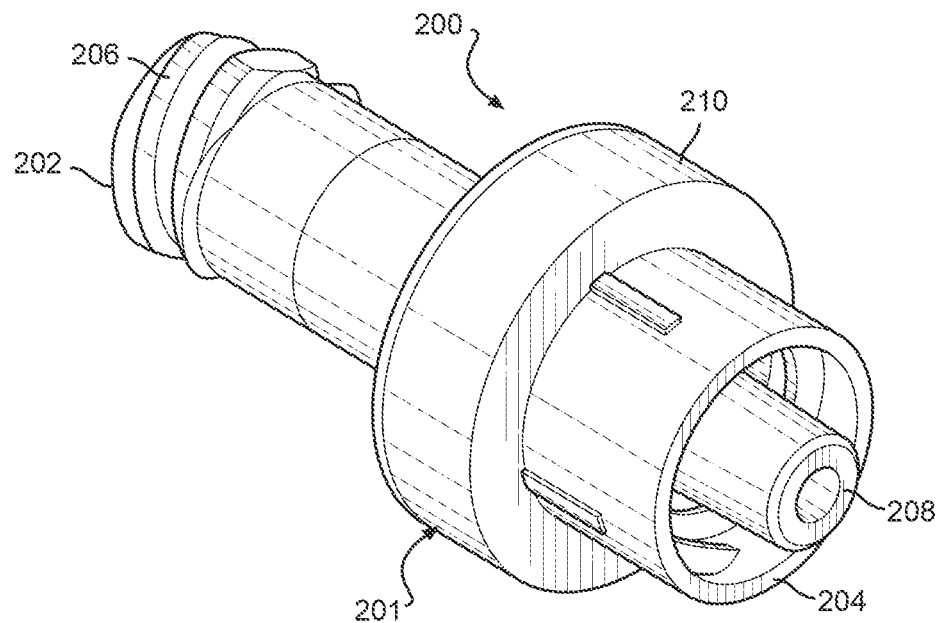
FIG. 10 illustrates a connector with integrated allergy testing in accordance with an embodiment of the invention.

FIG. 10 illustrates a connector design for the integrated testing system in accordance with an embodiment of the invention. The connector 200, includes a housing 201, having a proximal end 202 and a distal end 204, and can be configured for placement between a syringe body and a needle for the syringe. The connector 200 can be connected to the syringe body in a variety of different ways such as frictional hold, tabs, or any other suitable coupling. As illustrated in FIG. 10, the connector 200 can be coupled to the syringe via luer threads 206 positioned at the proximal end 202 of the connector 200. The connector 200 can also include a coupling 208 for coupling the connector 200 to a needle. The needle can take the form of a hypodermic-type needle or any other needle suitable for aspirating blood through the connector 200. The connector also includes a window 210 through which test strip (not shown) can be visualized.

Figure 11:
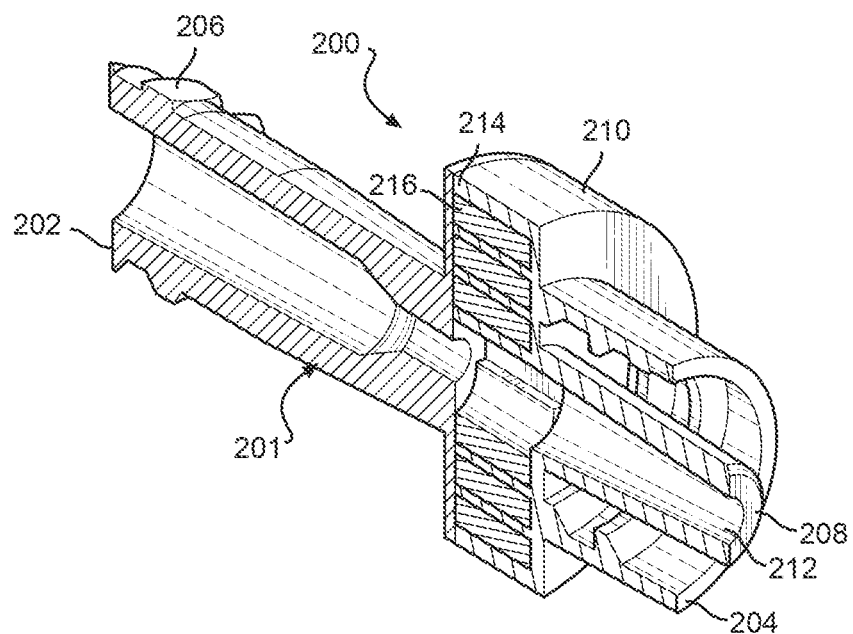
FIG. 11 illustrates a sectional view of the connector with integrated allergy testing illustrated in FIG. 10 in accordance with an embodiment of the invention.
Figure 12:
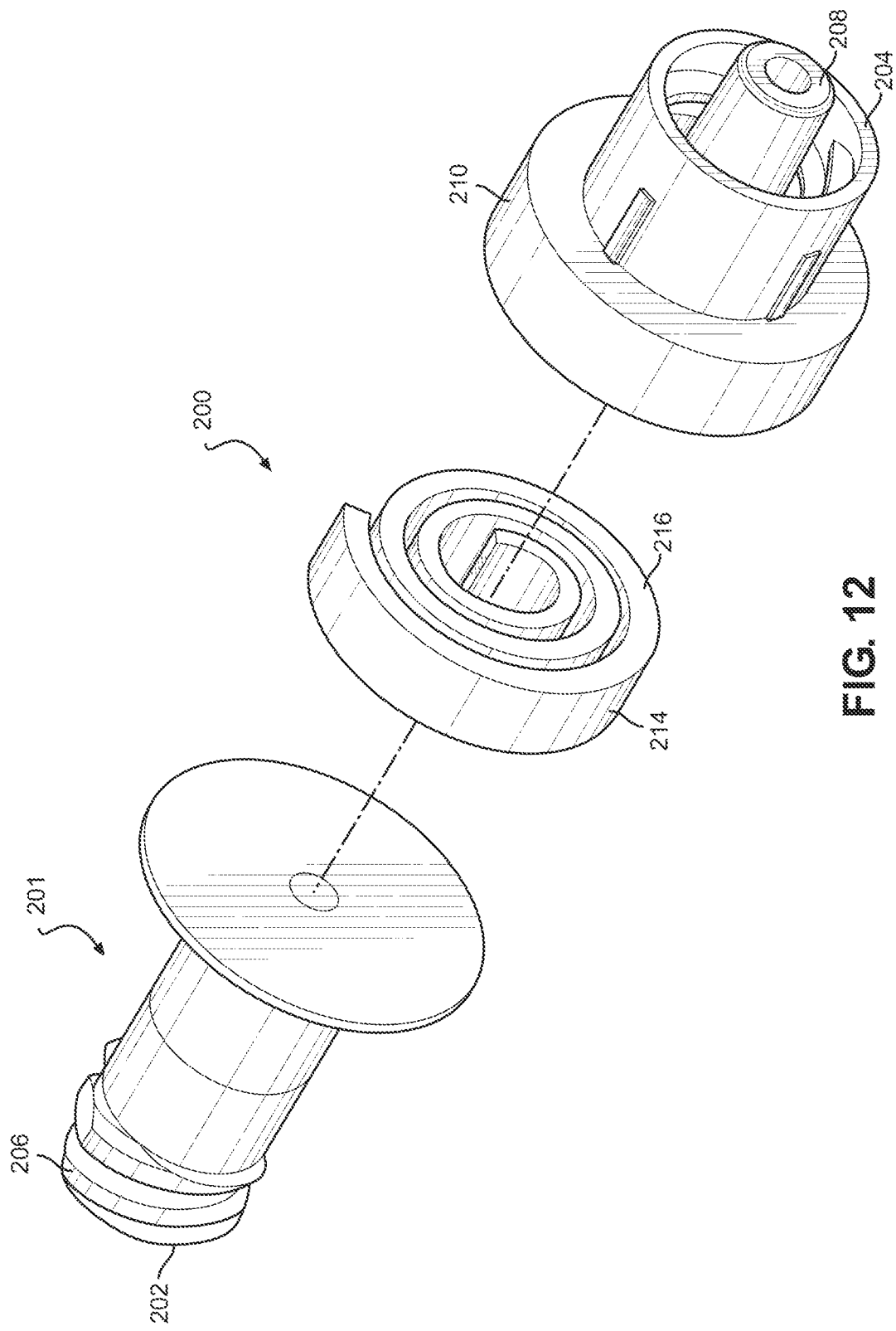
FIG. 12 illustrates an exploded view of the connector with integrated allergy testing illustrated in FIGS. 10 and 11 in accordance with an embodiment of the invention.

FIG. 11 illustrates a sectional view of the embodiment shown in FIG. 10 and FIG. 12 illustrates an exploded view of the embodiment illustrated in FIGS. 10 and 11. FIGS. 11 and 12 illustrate the test strip 214 disposed within the connector housing 201. As illustrated, the test strip 214 is spirally wound within the connector housing 201. The test strip 214 can be viewed through window 210 in the housing 201. Blood can be aspirated into a lumen 212 defined by housing 201, when testing is required. In addition, an absorbent pad 216 can be positioned beneath the test strip 214. The absorbent pad 216 integrated into the test strip 228 can absorb the plasma sample after the completion of the signal detection reaction. The absorbent pad 216 can also include a porous backing and an absorbent dispersed, adsorbed, or coated into the pores of the porous backing. A color signal can appear within approximately 10 minutes within the viewing window 210, but could take less time or more time depending on the antibodies contained in the blood sample.

Alternately test strip, for example, an immunochromatographic test strip, can be incorporated into a number of different medical devices. One such example is a test strip incorporated into a "hemo-hopper," such as a blood reservoir in a medical tray or kit. The blood aspirated during access to the vessel would be disposed into the hemo-hopper. The sample could then be absorbed into the test strip. In addition, an absorbent pad can be positioned beneath the test strip. The absorbent pad can absorb the plasma sample after the completion of the signal detection reaction. The absorbent pad can also include a porous backing and an absorbent dispersed, adsorbed, or coated into the pores of the porous backing. A color signal can appear within approximately 10 minutes, but could take less time or more time depending on the antibodies contained in the blood sample.

Figure 13A:
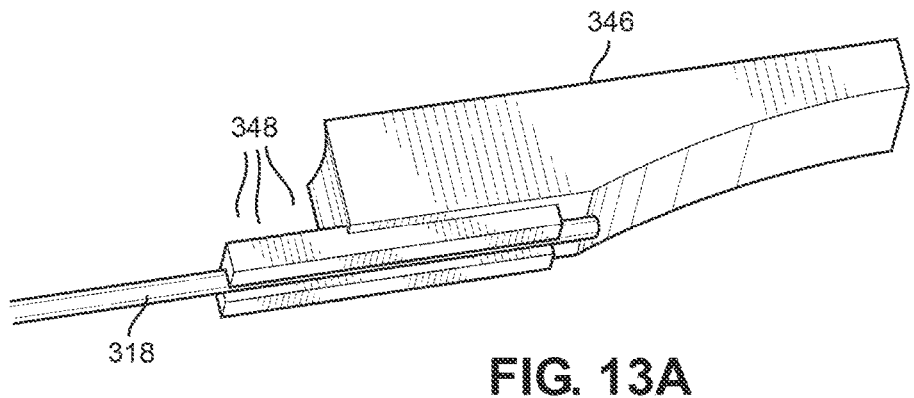
FIGS. 13A and 13B illustrate the cap that is a part of the module embodiment, and structures in the vicinity of the cap.
Figure 13B:
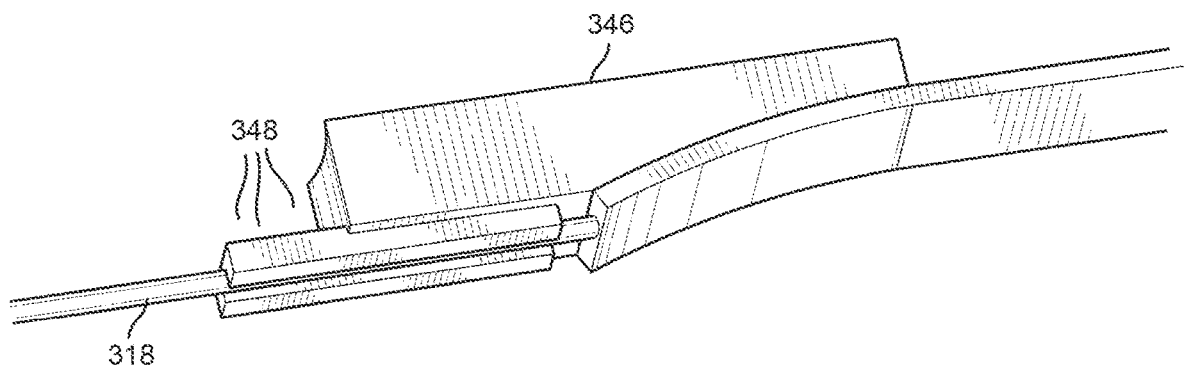

FIG. 13 (A, B) illustrates the end-cap that is a part of the module embodiment, and structures in the vicinity of the cap. The end-cap (346) is in contact with needle (318). The end-cap (346) defines part of cavity (348) where the vacuum button (32) can fit. A non-limiting embodiment of vacuum button (32) is shown in FIGS. 4-6. FIG. 13(A) shows cap without test strip, and FIG. 13 (B) shows cap with test strip.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention.

It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to falling within the scope of the invention.

What is claimed is:

1. A connector for indicating the presence of a substance in blood, the connector comprising:
   a housing having:
      a proximal end defining a proximal opening and a first channel, the proximal end having Luer threads configured to removably couple with a distal end of a medical device, and the first channel being in fluid communication with the medical device through the proximal opening when the proximal end is coupled to the medical device;
      a distal end defining a distal opening and a second channel, the distal end having a coupling configured to removably couple with a hub of a needle, the second channel being in fluid communication with the needle through the distal opening when the distal end is coupled to the hub of the needle, and
      a window defining a hollow interior for receiving withdrawn blood from the second channel that is received from the needle, the window being between the proximal and distal ends of the housing; and
   a test strip held within the hollow interior of the housing, the test strip being configured to produce a signal visible through the window that indicates the presence or absence of the substance in the withdrawn blood.

2. The connector of claim 1, wherein the window extends circumferentially about the housing.

3. The connector of claim 2, wherein the window extends radially beyond the proximal end of the housing and the distal end of the housing.

4. The connector of claim 1, wherein the distal end has an outer wall that is threaded.

5. The connector of claim 1, wherein the test strip is spirally wound within the hollow interior of the housing.

6. The connector of claim 1, further comprising an absorbent pad positioned beneath the test strip, the absorbent pad being configured to absorb the plasma of the withdrawn blood.

7. The connector of claim 1, wherein the test strip is an immunochromatographic test strip.

8. The connector of claim 1, wherein the medical device is a syringe, a trocar, a catheter, an introducer, a sheath, a pump, or a valve.

9. The connector of claim 8, wherein the medical device is the syringe.

10. The connector of claim 4, wherein the coupling is within the outer wall of the distal end.

11. A kit, comprising:
    a syringe comprising a plunger, the syringe having a distal end;
    a needle comprising a needle hub at its proximal end and a sharp tip at its distal end; and
    a connector for indicating the presence of a substance in blood, the connector comprising:
    a housing having:
       a proximal end defining a proximal opening and a first channel, the proximal end of the housing having Luer threads configured to removably couple with the distal end of the syringe, and the first channel being in fluid communication with the syringe through the proximal opening when the proximal end of the housing is coupled to the syringe;
       a distal end defining a distal opening and a second channel, the distal end of the housing having a coupling configured to removably couple with the needle, the second channel being in fluid communication through the distal opening with the needle when the distal end is coupled to the needle hub, and
       a window defining a hollow interior for receiving withdrawn blood from the second channel that is received from the needle, the window being between the proximal and distal ends of the housing; and
    a test strip held within the hollow interior of the housing, the test strip being configured to produce a signal visible through the window that indicates the presence or absence of the substance in the withdrawn blood.

12. The kit of claim 11, wherein the plunger is configured to produce negative pressure to urge the withdrawn blood into the hollow interior of the window.

13. The kit of claim 11, wherein the distal end has an outer wall that is threaded.

14. The kit of claim 13, wherein the coupling is within the outer wall of the distal end.

15. The kit of claim 11, wherein the window extends radially beyond the proximal end of the housing and the distal end of the housing.

16. A connector for indicating the presence of a substance in blood, the connector comprising:
    a housing having:
       a proximal end defining a proximal opening and a first channel, the proximal end configured to removably couple with a distal end of a medical device, and the first channel being in fluid communication with the medical device through the proximal opening when the proximal end is coupled to the medical device;
       a distal end defining a distal opening and a second channel, the distal end having a coupling configured to removably couple with a hub of a needle, the second channel being in fluid communication with the needle through the distal opening when the distal end is coupled to the hub of the needle, and
       a window extending circumferentially about the housing and defining a hollow interior for receiving withdrawn blood from the second channel that is received from the needle, the window being between the proximal and distal ends of the housing, and the window extending radially beyond the proximal and distal ends of the housing; and
    a test strip held within the hollow interior of the housing, the test strip being configured to produce a signal visible through the window that indicates the presence or absence of the substance in the withdrawn blood.

* * * * *